United States Patent [19]

Krüger et al.

[11] 4,314,839
[45] Feb. 9, 1982

[54] 1,2,3-THIADIAZOLE-5-CARBOXYLIC ACID AMIDE DERIVATIVES, PROCESS FOR MAKING THE SAME AND HERBICIDAL GROWTH REGULATING DEFOLIATING AND FUNGICIDAL COMPOSITIONS CONTAINING SAME

[75] Inventors: Hans-Rudolf Krüger; Friedrich Arndt; Dietrich Baumert; Reinhart Rusch, all of Berlin, Fed. Rep. of Germany

[73] Assignee: Schering Aktiengesellschaft, Berlin and Bergkamen, Fed. Rep. of Germany

[21] Appl. No.: 131,354

[22] Filed: Mar. 18, 1980

[30]  Foreign Application Priority Data

Apr. 5, 1979 [DE] Fed. Rep. of Germany ....... 2913977

[51] Int. Cl.³ .................. A01N 43/82; C07D 285/06; C07D 412/12
[52] U.S. Cl. .......................................... 71/73; 71/90; 542/421; 546/277; 548/127; 424/270; 424/263
[58] Field of Search ...................... 548/127; 71/90, 73; 542/421; 424/270

[56]  References Cited

U.S. PATENT DOCUMENTS 4,163,784  8/1979  Holland ............................... 548/127
4,177,054  12/1979  Arndt et al. ......................... 548/127

*Primary Examiner*—Alton D. Rollins
*Attorney, Agent, or Firm*—Michael J. Striker

[57]  ABSTRACT 1,2,3-Thiadiazole-5-carboxylic acid amide derivatives of the formula

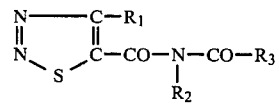

wherein $R_1$, $R_2$ and $R_3$ have the meaning indicated in the specification. Preferably, $R_1$ is methyl and $R_2$ is acetyl, chloroacetyl, propionyl, valeryl, cinnamoyl, cyclohexylcarbonyl, dichlorophenoxyacetyl, benzoyl, halobenzoyl, dichlorobenzoyl or methylbenzoyl, and $R_3$ is benzyl, halobenzyl, cyclohexyl, methylcyclohexyl or cyclohexylmethyl. The compounds have herbicidal, growth regulating, defoliating and fungicidal activity, although not all of these activities will be present in each of the compounds. The compounds are in addition highly selective against agriculturally valuable plants such as various grains, cotton, soybeans and plantation cultures.

45 Claims, No Drawings

1,2,3-THIADIAZOLE-5-CARBOXYLIC ACID AMIDE DERIVATIVES, PROCESS FOR MAKING THE SAME AND HERBICIDAL GROWTH REGULATING DEFOLIATING AND FUNGICIDAL COMPOSITIONS CONTAINING SAME

BACKGROUND OF THE INVENTION

The invention relates to 1,2,3-thiadiazole-5-carboxylic acid amide derivatives, a process for making the same and agents containing the same and having a herbicidal, growth regulating and defoliating as well as fungicidal activity.

In the area of plant production the weed control must meet three essential functions: it must safeguard the yields, assure the ultimate usefulness of the harvested products, and improve the working and production conditions. Modern weed control in many cases is the prerequisite for the complete mechanization of an organizational line or at least enables the possibility for the introduction of new techniques. Changes produced thereby have a strong effect on agricultural and horticultural operations. There is therefore heavy demand for both general as well as specific technical advances in the area of herbicides. This is particularly so because the heretofore known agents of this type do not fully comply with the requirements.

It is, therefore, an object of the present invention to provide for an agent which permits an improvement of the technique of weed control.

ESSENCE OF THE INVENTION

This object is met by an agent which at least contains one compound of the formula $$\begin{array}{c} N=\!=\!=\!C-R_1 \\ \| \quad\quad \| \\ N\diagdown_{S}\diagup C-CO-N-CO-R_3 \\ \quad\quad\quad | \\ \quad\quad\quad R_2 \end{array} \quad\quad I$$

In this formula $R_1$ is hydrogen or an alkyl group which in its chain may have one or several oxygen or sulfur atoms and which may be substituted by halogen, $R_2$ is hydrogen or $C_1$ to $C_{18}$-alkyl, $C_2$ to $C_8$-alkenyl, $C_2$ to $C_8$-alkinyl, aryl-$C_1$ to $C_3$-alkyl, all of which group may also be substituted, or is a $C_3$-$C_8$-cycloaliphatic hydrocarbon group which may also be substituted or in which there may be attached by condensation an aromatic or cycloaliphatic ring, or $R_2$ may be a $C_3$-$C_8$-cycloalkyl-$C_1$-$C_3$-alkyl group which may also be substituted. $R_2$ may further be an aromatic hydrocarbon residue which may be substituted in one or several places by $C_1$-$C_6$-alkyl and/or halogen and/or $C_1$-$C_6$-alkoxy and/or nitro and/or trifluoromethyl.

$R_3$ is hydrogen or one of the following radicals which may also be substituted: $C_1$-$C_{18}$-alkyl, $C_2$-$C_8$-alkenyl, aryl-$C_1$-$C_3$-alkyl or a $C_3$-$C_8$-cycloaliphatic hydrocarbon residue to which may be attached by condensation one or more aromatic or cycloaliphatic rings. $R_3$ may furthermore be an aromatic hydrocarbon residue which may also be substituted in one or several places by $C_1$-$C_6$-alkyl and/or $C_1$-$C_6$-alkoxy and/or nitro and/or trifluoromethyl or $R_3$ may be $C_1$-$C_6$-alkoxy, $C_3$-$C_6$-alkenyloxy or alkinyloxy or it may be aryloxy which may also be substituted, or $C_1$-$C_4$-alkylthio or arylthio which latter may also be substituted. $R_3$ may further be an amino group of the formula $$\begin{array}{c} R_4 \diagdown \\ \quad\quad N-, \\ R_5 \diagup \end{array}$$

in which $R_4$ and $R_5$ are the same or different and are hydrogen, $C_1$-$C_6$-alkyl, aryl or is aryl which may be substituted in one or several places by the same or different radicals selected from the group consisting of $C_1$-$C_6$-alkyl, halogen, $C_1$-$C_6$-alkoxy, nitro and/or trifluoromethyl.

These compositions surprisingly have a superior herbicidal activity, when applied to the soil or leaves, on seed weeds and resistant weeds and surpass the heretofore known compositions of an analogous constitution and a similar kind of activity.

The action of the compositions is partly systemic. They are particularly useful against dicotyledonous and monocotyledonous weeds of the genera Digitalis, Trifolium Portulaca, Papaver, Daucus, Kochia, Gypsophila, Lactuca, Solanum, Eschholtzia, Cheiranthus, Phacelia, Euphorbia, Linum, Convolvulus, Brassica, Datura, Cichorium, Ipomoea, Setaria, Agrostis, Phleum, Alopecurus, Phalaris, Dactylis, Festuca, Arrhenaterum, Lolium, Bromus, Avena, Allium, Cucumis, Medicago, Stellaria, Senecio, Matricaria, Lamium, Centaurea, Amaranthus, Galium, Chrysanthemum, Polygonum, Sorghum, Echinochloa, Digitaria, Cyperus, Poa and other weeds.

The amounts in which the compositions are employed against weeds are about 0.5 to 5.0 kg active agent per ha, 1 ha being equal to about 2.54 acres.

A selective weed control is for instance possible in cultures comprising cereals, cotton, soybeans and plantation cultures. These compositions have their greatest effect if they are applied by spraying to an emerged weed but may also be applied prior to its emergence. The weed cultures can also be drilled a few days after spraying.

The compositions may also be used to modify the natural development of the plants to obtain certain properties which may be useful in agricultural or horticultural respects. It will, however, be understood that not each composition has the same regulating effects with each type of plant, type of application, time of application or concentration of application.

The compounds of the invention can be applied to seeds, seedlings, prior or after emergence, to roots, stems, leaves, blossoms, fruits or other parts of the plants.

The control of the natural growth in general can be visually determined by modifications of the size, shape, color or structure of the treated plants or their parts.

By way of examples the following development changes of the plants may be effected by use of the compositions of the invention:

Enlargement of the leaf
Inhibition of the vertical growth
Inhibition of the root development
Stimulation of bud sprouting or the sprouting of plant stocks
Intensifying of the formation of plant dyestuffs
Defoliation.

It has also been found that the compounds of the invention are effective against various fungicidal pests, for instance of the genera Botrytis, Cercospora, Erysiphe, Helminthosporium, Piricularia, Plasmoparpa, Tilletia and others.

This has the advantage that simultaneously with the regulation of the plant growth a control of fungi which are pathogenic to the plants can be accomplished which is of substantial technical importance.

The compounds of the invention can be used either by themselves or in mixture with each other or in mixture with other active agents. If desired, other defoliating or plant protection agents or pesticides may be added as desired.

Should it be desirable to broaden the spectrum of the activity it is possible to add other biocidal agents. For instance, herbicidally active added agents may be added from the group of the triazines, aminotriazoles, anilides, diazines, uraciles, aliphatic carboxylic or halogenated carboxylic acids, substituted benzo acids and aryloxy carboxylic acids, hydrazides, amides, nitriles, esters of such carboxylic acids, carbamic- and thiocarbamic acid esters, urea derivatives, 2,3,6-trichlorobenzyloxypropanil, rhodan containing agents and other additives. Among further additives there may be named also nonphytotoxic additives which result in a synergistic increase of the activity with herbicides such as among others, wetting agents, emulsifiers, solvents, and oily additives.

The compounds of the invention or their mixtures are preferably used in the form of compositions such as powders, dusting agents, granulates, solutions, emulsions or suspensions and upon addition of liquid and/or solid carrier materials or diluents. If desired, wetting, adhesion, emulsification and/or dispersion promoting agents may be added.

Suitable liquid carrier materials are, for instance, water, aliphatic and aromatic hydrocarbons, such as, benzene, toluene, xylone, cyclohexanone, isophorone, dimethylsulfoxide, dimethylformamide, and furthermore mineral oil fractions.

As solid carrier materials there are suited mineral earths, for instance, tonsil, silicagel, talc, kaolin, attaclay, limestone, silicic acid and plant products such as flours.

As surface active agents which may be added there may be mentioned for instance calciumlignosulfonate, polyoxyethylene-alkylphenolether, naphthalene sulfonic acids and their salts, phenol sulfonic acids and their salts, formaldehyde condensation products, fatty alcohol sulfates as well as substituted benzosulfonic acids and their salts. The proportion of the agent or agents may be varied within broad ranges. The compositions may, for instance, contain about 5 to 95% by weight of active agents, about 95 to 5% by weight of liquid or solid carrier materials and, if desired, up to 20% by weight of surface active agents which would then reduce the amount of other carrier materials.

The application of the agents can be effected in conventional manner, for instance with water as the carrier material, in spray amounts of about 100 to 5000 1/ha. The application of the agents can be effected both in the so-called low volume and so-called ultra low volume process or also in the form of so-called micro granulates.

PREFERRED EMBODIMENTS

In the compounds indicated above by Formula 1, the different R radicals may, for instance, be:

$R_1$ may be hydrogen or $C_1$–$C_4$-alkyl, which may also be substituted, for instance, methyl, ethyl, propyl, chloromethyl, bromomethyl, methylthiomethyl, methoxymethyl.

$R_2$ may be hydrogen or $C_1$–$C_{18}$-alkyl, for instance methyl, ethyl, propyl, isopropyl, n-butyl, tert-butyl, 2,2-dimethyl-1-propyl, n-heptyl, n-nonyl, n-undecyl, n-octadecyl, 3-methylbutyl, 4-methyl-2-pentyl, isobutyl, 3,3-dimethylbutyl, 2-butyl, or 3,3-dimethyl-2-butyl; subsituted $C_1$–$C_{18}$-alkyl, for instance, 2-chloroethyl, 3-chloropropyl, 3-bromopropyl, 2-bromoethyl, 1-phenoxy-2-propyl, 3-dimethylaminopropyl, 2-dimethylaminoethyl, 3-diethylaminopropyl, tetrahydrofurfuryl, ethoxycarbonylmethyl, cyanomethyl, 2,2-dimethoxyethyl or 2-ethoxyethyl; $C_3$–$C_8$cycloalkyl-$C_1$–$C_3$-alkyl, for instance, cyclohexylmethyl, 4-cyanocyclohexylmethyl, 4-hydroxymethylcyclohexylmethyl, 4-carboxylcyclohexylmethyl, 1-hydroxycyclohexylmethyl, cycloheptylmethyl, cyclooctylmethyl or cyclopropylmethyl; $C_2$–$C_8$-alkenyl- or -alkinyl, for instance, 2-propenyl, 2-butenyl, 2-methyl-2-propenyl, 2-propinyl or 3-ethyl-1-pentyne-3-yl, aryl-$C_1$–$C_3$-alkyl, for instance, benzyl, 4-chlorobenzyl, 3-chlorobenzyl, 2-chlorobenzyl, 4-fluorobenzyl, 3-fluorobenzyl, 2-fluorobenzyl, 4-methylbenzyl, 3-methylbenzyl, 2-methylbenzyl, 3,4-methylendioxybenzyl, 2,4-dichlorobenzyl, 3,4-dichlorobenzyl, 4-methoxybenzyl, 3-methoxybenzyl, 2-methoxybenzyl, 2-pyridylmethyl, 3-pyridylmethyl, 4-pyridylmethyl, α,α,dimethylbenzyl, 1-phenylethyl, 2-phenylethyl, 1,2-diphenylethyl, 2,2-diphenylethyl, 4-fluoro-α-methoxybenzyl, 3-phenylpropyl or 2-furfuryl; $C_3$–$C_8$-cycloaliphatic hydrocarbon residue, for instance, cyclopropyl, cyclopentyl, cyclohexyl, 2-methylcyclohexyl, 3-methylcyclohexyl, 4-methylcyclohexyl, 1,2,3,4-tetrahydro-1-naphthyl, 1-ethinylcyclohexyl, cycloheptyl or cyclooctyl; aromatic hydrocarbon residues, for instance, phenyl, 3-chlorophenyl, 2-chlorophenyl, 4-chlorophenyl, 2,4-dichlorophenyl, 4-fluorophenyl, 2-methylphenyl, 3-methylphenyl, 4-methylphenyl, 1-naphthyl, 2-methoxyphenyl, 3-methoxyphenyl or 4-nitrophenyl.

$R_3$ may for instance comprise in case of the $C_1$–$C_{18}$-alkyl groups: methyl, ethyl, propyl, isopropyl, n-butyl, 1-ethylpropyl, tert-butyl, n-heptyl, n-nonyl, n-undecyl, n-octadecyl, 3,3-dimethylpropyl; in case of the substituted $C_1$–$C_{18}$-alkyl groups: chloromethyl, fluoromethyl, bromomethyl, 2-chloroethyl, 1-chloroethyl, dichloromethyl, trichloromethyl, 1-bromoethyl, phenoxymethyl, (2,4-dichlorophenoxy)-methyl, 1-phenoxyethyl, 2-phenoxyethyl; in case of the $C_2$–$C_8$-alkenyl groups: vinyl, 2-butenyl, 2-methyl-2 -propenyl, propene-1-yl, 2-phenylvinyl; in case of the $C_3$–$C_8$-cycloaliphatic hydrocarbon groups: cyclopropyl, cyclopentyl, cyclohexyl, methylcyclohexyl; in case of the aliphatic-aromatic hydrocarbon groups: benzyl, 4-chlorobenzyl, 1-phenylethyl, 2-phenylethyl; in case of the aromatic hydrocarbon groups: phenyl, 2-chlorophenyl, 4-chlorophenyl, 3-chlorophenyl, 2,6-dichlorophenyl, 2,4-dichlorophenyl, 2-methylphenyl, 3-methylphenyl, 4-methylphenyl, 3-nitrophenyl, 4-nitrophenyl, 2-methoxyphenyl, 4-methoxyphenyl, 1-naphthyl, 2-naphthyl or 2-furyl; in case of the $C_1$–$C_6$-alkoxy groups: methoxy, ethoxy, propoxy, isopropoxy, n-butoxy; in case of the $C_3$-$C_6$-alkenyl- or -alkinyloxy groups: 2-propeneyloxy, 2-buteneyloxy, 2-propinyloxy; in case of the aryloxy groups: phenoxy or 4-chlorophenoxy; in case of the arylthio groups: phenylthio or 4-chlorophenylthio; in case of the $C_1$-$C_4$-alkylthio groups: methylthio, ethylthio, propylthio; in case of the amino groups: methylamino, dimethylamino, ethylamino, diethylamino, anilino, N-methylanilino or 4-chloranilino.

Among the compounds of the invention those having a particularly superior herbicidal and growth regulating activity are those where in the above formula of the 1,2,3-thiadiazole-5-carboxylic acid amide derivatives the individual R groups are the following:

$R_1$ methyl $R_3CO$ acetyl, chloroacetyl, propionyl, valeryl, cinnamoyl, cyclohexylcarbonyl, dichlorophenoxyacetyl, benzoyl, halobenzoyl, dichlorobenzoyl or methylbenzoyl $R_2$ benzyl, halobenzyl, cyclohexyl, methylcyclohexyl or cyclohexylmethyl.

PROCESS OF MAKING

The compounds which so far have not been found in the literature can be made in various ways. In all of the processes presently to be described, $R_1$, $R_2$, and $R_3$ have the same meaning as in the above first-mentioned Formula I, while X is halogen, preferably chlorine and B is a univalent metal equivalent, preferably sodium, potassium or lithium.

Useful processes are the following:

(A) Metal compounds of the formula

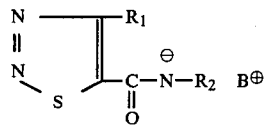

are reacted with acyl halides of the formula

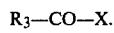

(B) 1,2,3-thiadiazole-5-carboxylic acid amides of the formula

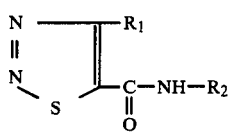

are reacted in the presence of acid acceptors with acyl halides of the formula $$R_3—CO—X$$

(C) 1,2,3-thiadiazole-5-carboxylic acid amides of the formula

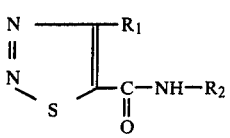

are reacted with acid anhydrides of the formula

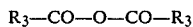

which reaction may be carried out in the presence of a catalyst such as sulfuric acid, p-toluenesulfonic acid or pyridine (D) 1,2,3-thiadiazole-5-carboxylic acid amides of the formula

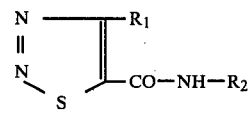

are reacted with isopropenyl compounds of the formula

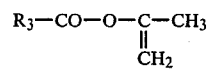

which reaction may also be carried out in the presence of a catalyst such as sulfuric acid, p-toluene sulfonic acid or pyridine, (E) 1,2,3-thiadiazole-5-carboximidochlorides of the formula

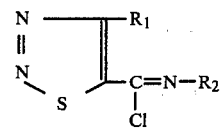

are reacted with carboxylic acids of the formula $$R_3—CO—OH$$

in the presence of an acid acceptor, (F) Metal compounds of the formula

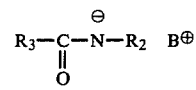

are reacted with 1,2,3-thiadiazole-5-carboxylic acid halides of the formula

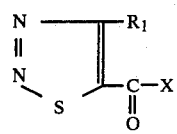

(G) Amides of the formula

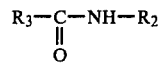

are reacted in the presence of acid acceptors with 1,2,3-thiadiazole-5-carboxylic acid halides of the formula

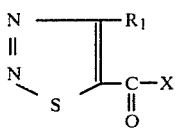

or (H) Imidochlorides of the formula $$R_3-C(Cl)=N-R_2$$

are reacted with 1,2,3-thiadiazole-5-carboxylic acids of the formula

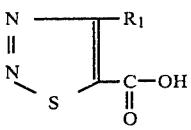

in the presence of acid acceptors.

In all these cases the reaction should be carried out at a temperature between 0° and 120° C., preferably between room temperature and the reflux temperature of the reaction mixture.

For the synthesis the reactants are preferably used in about equimolar amounts. Suitable reaction media are solvents which are inert in respect of the reactants. The selection of the solvents or suspension agents depends on the type of acyl halides, acid acceptors and metal compounds used.

As solvents or suspension agents there may for instance be mentioned the following: ethers like diethylether, tetrahydrofuran and dioxane; aliphatic and aromatic hydrocarbons, like petroleum ether, cyclohexane, benzene, toluene and xylene; carbonic acid nitriles, like acetonitrile, or ketones, like acetone.

As acid acceptors organic bases may be used, for instance triethylamine or N,N-dimethylaniline and pyridine bases or inorganic bases, like oxides, hydroxides and carbonates of alkaline earth and alkalimetals. Liquid bases like pyridine can also simultaneously be used as solvents.

The compounds made by any of the above processes can then be isolated in conventional form, for instance by distilling off the solvent at atmospheric or reduced pressure or by precipitation with water.

The compounds of the invention normally are colorless and nonsmelling crystalline substances or colorless and nonsmelling liquids which have a poor solubility in water, a moderate solubility in aliphatic hydrocarbons, such as petroleum ether and cyclohexane and a good solubility in halogenated hydrocarbons, such as chloroform and carbon tetrachloride; aromatic hydrocarbons, like benzene, toluene, xylene; ethers, like diethylether, tetrahydrofuran, and dioxane; carboxylic acid nitriles, like acetonitrile; ketones, like acetone; alcohols, like methanol and ethanol; carboxylic acid amides, like dimethylformamide and sulfoxides, like dimethylsulfoxides.

As solvents for the recrystallization there are preferred cyclohexane, acetonitrile and diisopropylether.

The starting products for making the compounds of the invention are known or can be made by an obvious procedure on the basis of the known processes.

EXAMPLES OF COMPOUNDS AND OF THE PROCESS OF MAKING

The following examples will further illustrate the making of the compounds of the invention and give certain examples of specific compounds.

EXAMPLE 1

4-methyl-1,2,3-thiadiazole-5-carboxylic acid-(N-acetyl-N-cyclohexylmethyl)-amide 16.8 g (0.07 mol) of 4-methyl-1,2,3-thiadiazole-5-carboxylic acid-(cyclohexylmethyl)-amide were suspended in 35 ml (0.32 mol) acetic acid isopropenyl ester and were reacted then with 0.04 ml concentrated sulfuric acid. The mixture was subsequently heated for 28 hours upon reflux. The remaining oil was crystallized with 50 ml of pentane. Recrystallization was effected with cyclohexane.

The yield was 14.7 g=74.6% of the theoretical value.
M.p.: 73°-74° C.—colorless crystals.

EXAMPLE 2

4-methyl-1,2,3-thiadiazole-5-carboxylic acid-(N-benzoyl-N-cyclohexylmethyl)-amide A solution of 23.9 g (0.1 mol) of 4-methyl-1,2,3-thiadiazole-5-carboxylic acid-(cyclohexylmethyl)-amide) in 200 ml of tetrahydrofuran was mixed with 2.4 g (0.1 mol) sodium hydride and maintained for 2 hours at reflux temperature. There were then added at 0°-10° C. upon cooling 14.06 g (0.1 mol) of benzoylchloride. After a reaction time of 2 hours the solution was concentrated and the resulting residue was cautiously reacted with water. Subsequently it was several times shaken out with ether. The ether extracts were dried on magnesium sulfate and concentrated and the remaining crystals were recrystallized from isopropyl ether.

The yield was 13.0 g–38% of the theoretical value
M.p.: 89°-91° C.—colorless crystals.

EXAMPLE 3

4-methyl-1,2,3-thiadiazole-5-carboxylic acid-(N-isobutyryl-N-cyclohexylmethyl)-amide 4.7 ml (0.05 mol) of isobutyric acid in 50 ml tetrahydrofuran were caused to boil with 7.1 ml (0.05 mol) of triethylamine. There were then added dropwise at the reflux temperature 12.9 g (0.05 mol) 4-methyl-1,2,3-thiadiazole-5-(N-cyclohexylmethylcarboximidochloride) dissolved in 100 ml tetrahydrofuran. The mass was then further heated upon reflux for 15 minutes. It was then permitted to cool; the precipitate was filtered off and the organic phase was concentrated. The remaining oil was taken up in ether and several times shaken out with water. The ether phase which had been dried on magnesium sulfate was concentrated and the remaining oil was dried in a vacuum at 40° C.

Yield: 11.0 g–71.2% of the theoretical value
$n_D^{20}$: 1.5291—colorless oil.

The following compounds of the invention were made in an analogous manner.

| Compound | Physical constants |
|---|---|
| 4-methyl-1,2,3-thiadiazole-5-carboxylic acid-(N-benzoyl-N- | |

| Compound | Physical constants |
|---|---|
| benzyl)-amide | m.p.: 95–97° C. |
| 4-methyl-1,2,3-thiadiazole-5-carboxylic acid-[N-benzoyl-N-(4-fluorobenzyl]-amide | m.p.: 143–44° C. |
| 4-methyl-1,2,3-thiadiazole-5-carboxylic acid-[N-benzoyl-N-(2-methylcyclohexyl)]-amide | m.p.: 99–102° C. |
| 4-methyl-1,2,3-thiadiazole-5-carboxylic acid-[N-acetyl-N-(2-fluorobenzyl)]-amide | $n_D^{20}$: 1,5627 |
| 4-methyl-1,2,3-thiadiazole-5-carboxylic acid-[N-acetyl-N-(4-fluorobenzyl)]-amide | $n_D^{20}$: 1,5625 |
| 4-methyl-1,2,3-thiadiazole-5-carboxylic acid-[N-acetyl-N-(4-chlorobenzyl)]-amide | m.p.: 66–68° C. |
| 4-methyl-1,2,3-thiadiazole-5-carboxylic acid-[N-(4-chlorobenzoyl-)-N-cyclohexylmethyl]-amide | m.p.: 115–16° C. |
| 4-methyl-1,2,3-thiadiazole-5-carboxylic acid-(N-propionyl-N-cyclohexylmethyl)-amide | m.p.: 64–65° C. |
| 4-methyl-1,2,3-thiadiazole-5-carboxylic acid-[N-(4-fluorobenzoyl)-N-cyclohexylmethyl]-amide | m.p.: 110–11° C. |
| 4-methyl-1,2,3-thiadiazole-5-carboxylic acid-(N-chloroacetyl-N-cyclohexylmethyl)-amide | m.p.: 111–12° C. |
| 4-methyl-1,2,3-thiadiazole-5-carboxylic acid-[N-(3-chlorobenzoyl)-N-cyclohexylmethyl]-amide | m.p.: 96–97° C. |
| 4-methyl-1,2,3-thiadiazole-5-carboxylic acid-[N-(3-methylbenzoyl)-N-cyclohexylmethyl]-amide | m.p.: 73–74° C. |
| 4-methyl-1,2,3-thiadiazole-5-carboxylic acid-[N-(4-methylbenzoyl)-N-cyclohexylmethyl]-amide | m.p.: 71–72° C. |
| 4-methyl-1,2,3-thiadiazole-5-carboxylic acid-(N-valeryl-N-cyclohexylmethyl)-amide | m.p.: 46–47° C. |
| 4-methyl-1,2,3-thiadiazole-5-carboxylic acid-[N-(2,4-dichlorophenoxyacetyl)-N-cyclohexylmethyl]-amide | m.p.: 87–89° C. |
| 4-methyl-1,2,3-thiadiazole-5-carboxylic acid-(N-benzoyl-N-cyclohexyl)-amide | m.p.: 81–83° C. |
| 4-methyl-1,2,3-thiadiazole-5-carboxylic acid-(n-acetyl-N-cyclohexyl)-amide | m.p.: 82–83° C. |
| 4-methyl-1,2,3-thiadiazole-5-carboxylic acid-[N-(2-chlorobenzoyl)-N-cyclohexylmethyl]-amide | m.p.: 53–55° C. |
| 4-methyl-1,2,3-thiadiazole-5-carboxylic acid-(N-cinnamoyl-N-cyclohexylmethyl)-amide | $n_{20}^{20}$: 1,5947 |
| 4-methyl-1,2,3-thiadiazole-5-carboxylic acid-(N-cyclohexylcarbonyl-N-cyclohexylmethyl)-amide | m.p.: 96–97° C. |
| 4-methyl-1,2,3-thiadiazole-5-carboxylic acid-(N-cyclohexylmethyl-N-cyclopropylcarbonyl)-amide | $n_D^{20}$: 1,5411 |
| 4-methyl-1,2,3-thiadiazole-5-carboxylic acid[N-cyclohexylmethyl-N-(2,6-dichlorobenzoyl)]-amide | m.p.: 81–83° C. |
| 4-methyl-1,2,3-thiadiazole-5-carboxylic acid-(N-cyclohexylmetnyl-N-dichloroacetyl)-amide | m.p.: 84–86° C. |
| 4-methyl-1,2,3-thiadiazole-5-carboxylic acid-(N-crotonoyl-N-cyclohexylmethyl)-amide | $n_D^{20}$: 1,5478 |
| 4-methyl-1,2,3-thiadiazole-5-carboxylic acid-[N-cyclohexylmethyl-N-(2-furoyl)]-amide | m.p.: 80–81° C. |
| 4-methyl-1,2,3-thiadiazole-5-carboxylic acid-[N-cyclohexylmethyl]N-(2,4-dichlorobenzoyl)]-amide | m.p.: 87–88° C. |
| 4-methyl-1,2,3-thiadiazole-5-carboxylic acid-[N-cyclohexylmethyl-N-(2-trifluoromethylbenzoyl)]-amide | m.p.: 63–64° C. |
| 4-methyl-1,2,3-thiadiazole-5-carboxylic acid-[N-cyclohexylmethyl]N-(3,6-dichloro-2-methoxybenzoyl)]-amide | m.p.: 76–77° C. |
| 4-methyl-1,2,3-thiadiazole-5-carboxylic acid-[N-cyclohexylmethyl-N-(3-triflurormethylbenzoyl)]-amide | m.p.: 92–93° C. |
| 4-methyl-1,2,3-thiadiazole-5-carboxylic acid-[N-cyclohexylmethyl-N-(3-furoyl)]-amide | m.p.: 86–88° C. |
| 4-methyl-1,2,3-thiadiazole-5-carboxylic acid-[N-cyclohexylmethyl-N-(2,5-dichlorobenzoyl)]-amide | m.p.: 67–69° C. |
| 4-methyl-1,2,3-thiadiazole-5-carboxylic acid-[N-cyclohexylmethyl-N-(3,5-dichlorobenzoyl)]-amide | m.p.: 67–69° C. |
| 4-methyl-1,2,3-thiadiazole-5-carboxylic acid-[N-cyclohexylmethyl-N-(2-phenoxybenzoyl)]-amide | m.p.: 91–93° C. |
| 4-methyl-1,2,3-thiadiazole-5-carboxylic acid-[N-cyclohexylmethyl-N-(4-methyl-1,2,3-thiadiazole-5-ylcarbonyl)]-amide | m.p.: 64–67° C. |
| 4-methyl-1,2,3-thiadiazole-5-carboxylic acid-[4-cyclohexylmethyl-N-(3,4-dichlorobenzoyl)]-amide | m.p.: 113–114° C. |
| 4-methyl-1,2,3-thiadiazole-5-carboxylic acid-[N-acetyl-N-(3-methylcyclohexyl)]-amide | m.p.: 68–70° C. |

STARTING PRODUCT

By way of example the making of one of the starting products used in the processes for making the compounds of the invention is done as follows:

4-methyl-1,2,3-thiadiazole-5-(N-cyclohexylmethylcarboximidechloride 47.8 g (0.2 mol) of 4-methyl-1,2,3-thiadiazole-5-carboxylic acid-(cyclohexylmethyl)-amide, dissolved in 100 ml toluene were reacted at room temperature with 41.6 (0.02 mol) of phosphorus pentachloride and subsequently heated for 1 hour from reflux. The solution was then concentrated and the remaining oil was digested with cyclohexane. Recrystallization was effected from cyclohexane.

Yield: 40.0 g=77.5% of the theoretical value

M.p.: 51°–52° C.—colorless crystals.

USES AND ACTIVITIES

The following examples will further explain the use and activity and superiority of the compounds of the invention.

EXAMPLE 4

The compounds listed in the table below were sprayed in a hothouse in the form of an aqueous emulsion or suspension in amounts of 5 kg of active agent/ha in 600 liters water/ha. The test plants sprayed were the following: Sinapis (Si), Solanum (So), Beta vulgaris (Be), Gossypium (Go), Hordeum (Ho), Zea mays (Ze), Lolium (Lo), and Setaria (Se). The application was effected either in preemergence application (V) or in postemergence application (N). An evaluation of the results was effected 3 weeks after the treatment on a scale from 0 to 4 as follows:

| Compounds | Si V | Si N | So V | So N | Be V | Be N | Go V | Go N | Ho V | Ho N | Ze V | Ze N | Lo V | Lo N | Se V | Se N |
|---|---|---|---|---|---|---|---|---|---|---|---|---|---|---|---|---|
| 4-methyl-1,2,3-thiadiazole-5-carboxylic acid-(N-acetyl-N-cyclohexylmethyl)-amide | 4 | 4 | 4 | 4 | 4 | 4 | 3 | 4 | 3 | 2 | 2 | 2 | 4 | 3 | 4 | 4 |
| 4-methyl-1,2,3-thiadiazole-5-carboxylic acid-(N-benzoyl-N-cyclohexylmethyl)-amide | 4 | 4 | 3 | 3 | 3 | 4 | 2 | 2 | 2 | 1 | 2 | 1 | 3 | 1 | 2 | 4 |
| 4-methyl-1,2,3-thiadiazole-5-carboxylic acid-(N-isobutyryl-N-cyclohexylmethyl)-amide | 3 | 4 | 3 | 4 | 3 | 4 | 2 | 4 | 3 | 0 | 2 | 0 | 2 | 1 | 2 | 4 |
| 4-methyl-1,2,3-thiadiazole-5-carboxylic acid-(N-benzoyl-N-benzyl)-amide | 0 | 3 | 0 | 2 | 0 | 2 | 0 | 1 | 0 | 1 | 0 | 1 | 0 | 0 | 0 | 4 |
| 4-methyl-1,2,3-thiadiazole-5-carboxylic acid-[N-benzoyl-N-(4-fluorobenzyl)]-amide | 0 | 1 | 0 | 1 | 0 | 1 | 0 | 0 | 0 | 0 | 0 | 0 | 0 | 0 | 0 | 1 |
| 4-methyl-1,2,3-thiadiazole-5-carboxylic acid-[N-benzoyl-N-(2-methylcyclohexyl)]-amide | 0 | 1 | 0 | 1 | 0 | 1 | 0 | 1 | 0 | 1 | 0 | 1 | 0 | 1 | 0 | 1 |
| 4-methyl-1,2,3-thiadiazole-5-carboxylic acid-[N-acetyl-N-(2-fluorobenzyl)]-amide | 0 | 4 | 0 | 3 | 0 | 3 | 0 | 3 | 0 | 1 | 0 | 0 | 0 | 1 | 0 | 4 |
| 4-methyl-1,2,3-thiadiazole-5-carboxylic acid-[N-acetyl-N-(4-fluorobenzyl)]-amide | 0 | 4 | 0 | 3 | 0 | 3 | 0 | 3 | 0 | 1 | 0 | 1 | 0 | 2 | 0 | 4 |
| 4-methyl-1,2,3-thiadiazole-5-carboxylic acid-[N-acetyl-N-(4-chlorobenzyl)]-amide | 1 | 4 | 0 | 2 | 0 | 2 | 0 | 1 | 0 | 0 | 0 | 0 | 0 | 0 | 0 | 4 |
| 4-methyl-1,2,3-thiadiazole-5-carboxylic acid-]N-(4-chlorobenzoyl)-N-cyclohexylmethyl]-amide | 0 | 3 | 0 | 0 | 0 | 0 | 0 | 0 | 0 | 1 | 0 | 0 | 0 | 0 | 0 | 3 |
| 4-methyl-1,2,3-thiadiazole-5-carboxylic acid-(N-propionyl-N-cyclohexylmethyl)-amide | 3 | 4 | 3 | 3 | 1 | 4 | 0 | 4 | 3 | 1 | 1 | 1 | 1 | 1 | 2 | 4 |
| 4-methyl-1,2,3-thiadiazole-5-carboxylic acid-[N-(4-fluorobenzoyl)-N-cyclohexylmethyl]-amide | 0 | 2 | 0 | 0 | 0 | 2 | 0 | 0 | 0 | 0 | 0 | 0 | 0 | 0 | 0 | 2 |
| 4-methyl-1,2,3-thiadiazole-5-carboxylic acid-(N-chloroacetyl-N-cyclohexylmethyl)-amide | 4 | 4 | 4 | 4 | 4 | 4 | 3 | 4 | 4 | 1 | 3 | 1 | 4 | 3 | 4 | 4 |
| 4-methyl-1,2,3-thiadiazole-5-carboxylic acid-[N-(3-chlorobenzoyl)-N-cyclohexylmethyl]-amide | 0 | 3 | 1 | 1 | 0 | 1 | 0 | 2 | 0 | 0 | 0 | 0 | 0 | 1 | 1 | 2 |
| 4-methyl-1,2,3-thiadiazole-5-carboxylic acid-[N-(3-methylbenzoyl-N-cyclohexylmethyl)]-amide | 0 | 4 | 1 | 3 | 0 | 1 | 0 | 2 | 1 | 0 | 0 | 0 | 1 | 0 | 1 | 3 |
| 4-methyl-1,2,3-thiadiazole-5-carboxylic acid-[N-(4-methylbenzoyl)-N-cyclohexylmethyl]-amide | 1 | 3 | 1 | 3 | 0 | 1 | 0 | 1 | 0 | 1 | 0 | 0 | 0 | 1 | 0 | 3 |
| 4-methyl-1,2,3-thiadiazole-5-carboxylic acid-(N-valeryl-N-cyclohexylmethyl)-amide | 4 | 4 | 4 | 3 | 4 | 4 | 3 | 4 | 3 | 1 | 2 | 1 | 3 | 2 | 4 | 4 |
| 4-methyl-1,2,3-thiadiazole-5-carboxylic acid-[N-(2,4-dichlorophenoxyacetyl)-N-cyclohexylmethyl]-amide | 4 | 4 | 4 | 4 | 4 | 4 | 3 | 3 | 3 | 0 | 3 | 1 | 4 | 1 | 4 | 4 |
| 4-methyl-1,2,3-thiadiazole-5-carboxylic acid-(N-benzoyl-N-cyclohexyl)-amide | 0 | 1 | 0 | 2 | 0 | 2 | 0 | 0 | 0 | 0 | 0 | 0 | 0 | 0 | 0 | 2 |
| 4-methyl-1,2,3-thiadiazole-5-carboxylic acid-(N-acetyl-N-cyclohexyl)-amide | 0 | 1 | 1 | 1 | 0 | 1 | 0 | 1 | 1 | 1 | 0 | 1 | 0 | 0 | 0 | 1 |
| 4-methyl-1,2,3-thiadiazole-5-carboxylic acid-[N(2-chlorobenzoyl)-N-cyclohexylmethyl]-amide | 0 | 1 | 0 | 1 | 1 | 2 | 0 | 1 | 0 | 0 | 0 | 1 | 0 | 1 | 0 | 2 |
| 4-methyl-1,2,3-thiadiazole-5-carboxylic acid-(N-cinnamoyl-N-cyclohexylmethyl)-amide | 2 | 3 | 3 | 3 | 3 | 4 | 2 | 2 | 1 | 2 | 0 | 1 | 3 | 3 | 3 | 4 |
| 4-methyl-1,2,3-thiadiazole-5-carboxylic acid-(N-cyclohexylcarbonyl-N-cyclohexylmethyl)-amide | 0 | 1 | 1 | 1 | 2 | 2 | 0 | 1 | 0 | 1 | 0 | 0 | 1 | 0 | 0 | 1 |
| 4-methyl-1,2,3-thiadiazole-5-carboxylic acid-(N-cyclohexylmethyl-N-cyclopropylcarbonyl)-amide | 4 | 4 | 3 | 3 | 3 | 4 | 2 | 2 | 2 | 1 | 0 | 0 | 1 | 2 | 3 | 4 |
| 4-methyl-1,2,3-thiadiazole-5-carboxylic acid-[N-cyclohexylmethyl-N-(2,6-dichlorobenzoyl)]-amide | 3 | 2 | 3 | 3 | 3 | 4 | 2 | 2 | 1 | 1 | 1 | 1 | 1 | 2 | 3 | 4 |
| 4-methyl-1,2,3-thiadiazole-5- | | | | | | | | | | | | | | | | |

-continued

| Compounds | Si V | Si N | So V | So N | Be V | Be N | Go V | Go N | Ho V | Ho N | Ze V | Ze N | Lo V | Lo N | Se V | Se N |
|---|---|---|---|---|---|---|---|---|---|---|---|---|---|---|---|---|
| carboxylic acid-(N-cyclohexylmethyl-N-dichloroacetyl)-amide | 4 | 4 | 4 | 3 | 4 | 4 | 3 | 4 | 4 | 2 | 3 | 2 | 4 | 3 | 4 | 4 |
| 4-methyl-1,2,3-thiadiazole-5-carboxylic acid-(N-crotonoyl-N-cyclohexylmethyl)-amide | 4 | 4 | 4 | 3 | 2 | 3 | 3 | 4 | 3 | 1 | 2 | 0 | 4 | 1 | 3 | 3 |
| 4-methyl-1,2,3-thiadiazole-5-carboxylic acid-[(N-cyclohexylmethyl-N-(2-furoyl)]-amide | 2 | 4 | 3 | 3 | 2 | 4 | 0 | 3 | 0 | 3 | 2 | 0 | 3 | 0 | 3 | 2 |
| 4-methyl-1,2,3-thiadiazole-5-carboxylic acid-[(N-cyclohexylmethyl-N-(2,4-dichlorobenzoyl)]-amide | 1 | 1 | 1 | 1 | 0 | 0 | 0 | 0 | 0 | 0 | 0 | 0 | 0 | 0 | 0 | 0 |
| 4-methyl-1,2,3-thiadiazole-5-carboxylic acid-[N-cyclohexylmethyl-N-(2-trifluoromethylbenzoyl]-amide | 0 | 0 | 0 | 0 | 0 | 0 | 0 | 1 | 0 | 0 | 0 | 0 | 0 | 0 | 0 | 1 |
| 4-methyl-1,2,3-thiadiazole-5-carboxylic acid-[N-cyclohexylmethyl-N-(3,6-dichloro-2-methoxybenzoyl)]-amide | 3 | 3 | 3 | 3 | 3 | 3 | 2 | 4 | 2 | 0 | 1 | 1 | 2 | 0 | 1 | 2 |
| 4-methyl-1,2,3-thiadiazole-5-carboxylic acid-[N-cyclohexylmethyl-N-(3-trifluoromethylbenzoyl)]-amide | 1 | 3 | 2 | 2 | 0 | 1 | 0 | 2 | 0 | 0 | 0 | 0 | 0 | 0 | 0 | 1 |
| 4-methyl-1,2,3-thiadiazole-5-carboxylic acid-[N-cyclohexylmethyl-N-(3-furoyl)]-amide | 2 | 4 | 4 | 2 | 0 | 3 | 0 | 2 | 2 | 0 | 0 | 0 | 0 | 1 | 2 | 0 |
| 4-methyl-1,2,3-thiadiazole-5-carboxylic acid-[N-cyclohexylmethyl-N-(2,5-dichlorobenzoyl)]-amide | 0 | 1 | 0 | 1 | 0 | 1 | 0 | 0 | 0 | 0 | 0 | 0 | 0 | 0 | 0 | 0 |
| 4-methyl-1,2,3-thiadiazole-5-carboxylic acid-[N-cyclohexylmethyl-N-(3,5-dichlorobenzoyl)]-amide | 2 | 1 | 4 | 2 | 2 | 0 | 0 | 0 | 1 | 0 | 1 | 0 | 2 | 0 | 2 | 0 |
| 4-methyl-1,2,3-thiadiazole-5-carboxylic acid-[N-cyclohexylmethyl-N-(2-phenoxybenzoyl)]-amide | 0 | 1 | 0 | 1 | 0 | 1 | 0 | 0 | 0 | 0 | 0 | 0 | 0 | 0 | 0 | 0 |
| 4-methyl-1,2,3-thiadiazole-5-carboxylic acid-[N-cyclohexylmethyl-N-(4-methyl-1,2,3-thiadiazole-5-ylcarbonyl)]-amide | 4 | 4 | 4 | 4 | 4 | 4 | 4 | 4 | 4 | 4 | 3 | 4 | 4 | 4 | 4 | 4 |
| 4-methyl-1,2,3-thiadiazole-5-carboxylic acid-[N-cyclohexylmethyl-N-(3,4-dichlorobenzoyl)]-amide | 4 | 4 | 4 | 4 | 4 | 4 | 4 | 4 | 4 | 4 | 3 | 3 | 4 | 4 | 4 | 4 |
| 4-methyl-1,2,3-thiadiazole-5-carboxylic acid-[N-acetyl-N-(3-methylcyclohexyl)]-amide | 4 | 4 | 4 | 4 | 4 | 4 | 4 | 4 | 4 | 4 | 4 | 3 | 4 | 4 | 4 | 4 |
| Untreated | 0 | 0 | 0 | 0 | 0 | 0 | 0 | 0 | 0 | 0 | 0 | 0 | 0 | 0 | 0 | 0 |

0 = no effects
1-2 = growth regulating effect in the form of an intensive coloration of the leaves, retardation, growth depression and smaller or larger size of the leaves as well as low root development.
3-4 = these plants were no longer viable or were withered.

EXAMPLE 5

The plants listed below were treated in a hothouse prior to emergence with the indicated compound in an amount of 1 kg of active agent/ha. The compound was applied for this purpose as a suspension in 500 liters of water/ha to the soil and the application was effected in a uniform manner. The results show that the compounds of the invention destroyed widespread weeds while they left without damage the economically important soybeans.

The results were recorded on a scale from 0 to 10 in which 0 indicated total destruction of the plants and 10 indicated no damage to the plants.

| Compound | soybeans | Ipomoea | Avena | Alopecurus | Echinochloa | Setaria | Digitaria | Poa | Solanum | Datura | Escholtzia | Kochia |
|---|---|---|---|---|---|---|---|---|---|---|---|---|
| 4-methyl-1,2,3-thiadiazole-5-carboxylic acid-(N-acetyl-N-cyclohexylmethyl)-amide | 10 | 0 | 0 | 0 | 0 | 0 | 0 | 0 | 0 | 0 | 0 | 0 |
| Untreated | 10 | 10 | 10 | 10 | 10 | 10 | 10 | 10 | 10 | 10 | 10 | 10 |

EXAMPLE 6

Cucumbers were treated in a hothouse prior to emergence with the compound listed below in amounts of 0.3 kg, 1 kg and 3 kg/ha. The active agents for this purpose were applied as a 20% emulsion concentrate in an aqueous emulsion with an amount of liquid of 500 liters spray per hectare. 3 weeks after treatment the growth regulating effect was determined by measuring the length and width of the first foliage leaf. The results of the measurement were related to those obtained in untreated control plants. As appears from the measurements the treatment with the compound of the invention resulted in a great enlargement of the leaf. Besides, the treated plants were of a more intensive green.

| Compound | active agent kg/ha | length of leaf in % | width of leaf in % |
|---|---|---|---|
| 4-methyl-1,2,3-thia-diazole-5-carboxylic acid-(N-acetyl-N-cyclohexylmethyl)-amide | 0.3 | 110 | 107 |
| | 1.0 | 124 | 130 |
| | 3.0 | 133 | 151 |
| Untreated | — | 100 | 100 |

EXAMPLE 7

Effects of a prophylactic leaf treatment of grapevines against *Plasmopara viticola*

Young grapevines with about 5 to 8 leaves were sprayed in a hothouse with the compounds listed below in the concentrations indicated. After the spray deposit had been dried the bottom side of the leaves was sprayed with an aqueous emulsion of sporangia of the above-indicated fungus (about 20,000 per ml). The plants were then immediately incubated in a hothouse at 22° to 24° C. and in as high a water-saturated atmosphere as possible.

Starting with the second day the air humidity was reduced for 3 to 4 days to a normal level (30 to 70% saturation) followed by another day in water vapor saturation. Following this treatment the percentage portion of the fungus infected surface of each leaf was noted and the average obtained per treatment was saturated as follows in order to determine the fungicidal activity:

$$100 - \frac{100 \cdot \text{infestation of treated plants}}{\text{infestation of untreated plants}} = \% \text{ activity}$$

The active agents were applied in the form of a 20% spray powder.

| Compound | results after treatment with following percentage of compound | |
|---|---|---|
| | 0.025 | 0.005 |
| 4-methyl-1,2,3-thiadiazole-5-carboxylic acid-(N-benzoyl-N-cyclohexylmethyl)-amide | 100 | 95 |
| 4-methyl-1,2,3-thiadiazole-5-carboxylic acid-(N-benzoyl-N-benzyl)-amide | 100 | 49 |
| 4-methyl-1,2,3-thiadiazole-5-carboxylic acid-[N-benzoyl-N-(2-methylcyclohexyl)]-amide | 77 | |
| 4-methyl-1,2,3-thiadiazole-5-carboxylic acid-[N-acetyl-N-(2-fluorobenzyl)]-amide | 97 | |
| 4-methyl-1,2,3-thiadiazole-5-carboxylic acid-[N-acetyl-N-(4-fluorobenzyl)]-amide | 73 | |
| 4-methyl-1,2,3-thiadiazole-5-carboxylic acid-[N-acetyl-N-(4-chlorobenzyl)]-amide | 78 | |
| 4-methyl-1,2,3-thiadiazole-5-carboxylic acid-(N-chloroacetyl-N-cyclohexylmethyl)-amide | 97 | |
| 4-methyl-1,2,3-thiadiazole-5-carboxylic acid-(N-valeryl-N-cyclohexylmethyl)-amide | 99 | |
| 4-methyl-1,2,3-thiadiazole-5-carboxylic acid-[N-(2-chlorobenzoyl)-N-cyclohexylmethyl]-amide | 75 | |
| 4-methyl-1,2,3-thiadiazole-5-carboxylic acid-(N-cinnamoyl-N-cyclohexylmethyl)-amide | 75 | |
| 4-methyl-1,2,3-thiadiazole-5-carboxylic acid-(N-cyclohexylmethyl-N-cyclopropylcarbonyl)-amide | 70 | |
| 4-methyl-1,2,3-thiadiazole-5-carboxylic acid-[N-cyclohexylmethyl-N-(2,6-dichlorobenzoyl)]-amide | 75 | |

EXAMPLE 8

Effect of the prophylactic leaf treatment of pumpkin plants against *Erysiphe cichoracearum*

The compounds noted below were sprayed in the indicated concentrations on young pumpkin plants until they were dripping wet.

After the spray deposits had been dried the plants were inoculated by being dusted with dry mildew spores of *Erysiphe cichoracearum* at a temperature of 24° C.

After a week the infested mildew surface in percentage was determined relative to the total leaf surface. The fungicidal activity was calculated as follows:

$$100 - \frac{100 \cdot \text{infestation of treated plants}}{\text{infestation of untreated plants}} = \% \text{ activity}$$

The active compounds were applied in the form of a 20% spray powder.

| Compound | results after treatment with following percentage of compound | |
|---|---|---|
| | 0.025 | 0.005 |
| 4-methyl-1,2,3-thiadiazole-5-carboxylic acid-(N-acetyl-N-cyclohexylmethyl)-amide | 100 | 92 |
| 4-methyl-1,2,3-thiadiazole-5-carboxylic acid-(N-benzoyl-N-cyclohexylmethyl)-amide | 70 | |
| 4-methyl-1,2,3-thiadiazole-5-carboxylic acid-(N-isobutyryl-N-cyclohexylmethyl)-amide | 100 | 93 |
| 4-methyl-1,2,3-thiadiazole-5-carboxylic acid-(N-propionyl-N-cyclohexylmethyl)-amide | 85 | 60 |
| 4-methyl-1,2,3-thiadiazole-5-carboxylic acid-(N-chloroacetyl-N-cyclohexylmethyl)-amide | 99 | 85 |
| 4-methyl-1,2,3-thiadiazole-5-carboxylic acid-(N-valeryl-N-cyclohexylmethyl)-amide | 100 | 90 |
| 4-methyl-1,2,3-thiadiazole-5-carboxylic acid-[N-(2,4-dichlorophenoxyacetyl)-N-cyclohexylmethyl]-amide | 60 | |
| 4-methyl-1,2,3-thiadiazole-5-carboxylic acid-(N-cyclohexylmethyl-N-cyclopropylcarbonyl)-amide | 80 | |

It is noted that none of the treatments did any damage to the pumpkin plants.

EXAMPLE 9

**Effect of leaf treatment of rice seedlings against *Piricularia oryzae***

Young rice seedlings were sprayed with the compounds listed below in the indicated amounts until they were dripping wet. After drying of the spray deposits the treated plants and untreated control plants were inoculated by being sprayed with a suspension of spores (about 200,000/ml) of the fungus that causes the leaf spot disease, *Piricularia oryzae*. The incubation was carried out of the wet plants in a hothouse at +25° to +27° C.

After 5 days it was determined which percentage of the leaf surface had been infested. From the figures obtained the fungicidal activity was determined as follows:

$$100 - \frac{100 \cdot \text{infestation of treated plants}}{\text{infestation of untreated plants}} = \% \text{ activity}$$

The active agents were applied in the form of a 20% spray powder.

| Compound | results after treatment with following percentage of compound 0.1 |
|---|---|
| 4-methyl-1,2,3-thiadiazole-5-carboxylic acid-(N-benzoyl-N-cyclohexylmethyl)-amide | 75 |
| 4-methyl-1,2,3-thiadiazole-5-carboxylic acid-(N-benzoyl-N-benzyl)-amide | 90 |
| 4-methyl-1,2,3-thiadiazole-5-carboxylic acid-[N-benzoyl-N-(2-methylcyclohexyl]-amide | 75 |
| 4-methyl-1,2,3-thiadiazole-5-carboxylic acid-(N-chloroacetyl-N-cyclohexylmethyl)-amide | 90 |

It is noted that none of the rice plants was damaged by the treatment.

EXAMPLE 10

**Effect of seed treatment of barley against *Helminthosporium spec***

Barley seeds which had a natural infestation by Helminthosporium gramineum were in some cases left untreated and in other cases treated with the compound as indicated in the table below and were seeded in plant pots filled with earth. The germination was effected at temperatures below +16° C. After emergence the seedlings were exposed daily for 12 hours to artificial light. After about 5 weeks all emerged plants including the fungus infected plants were counted as per each test plant. The fungicidal activity was calculated as follows:

$$100 - \frac{100 \cdot \text{infestation of treated plants}}{\text{infestation of untreated plants}} = \% \text{ activity}$$

The compounds were applied in the form of a 20% spray powder.

| Compound | % effect with following amounts (in g) of active agent per 100 kg of seed material | | | | |
|---|---|---|---|---|---|
| | 10 | 2 | 13.1 | 5.3 | 2.6 |
| 4-methyl-1,2,3-thiadiazole-5-carboxylic acid-(N-acetyl-N-cyclohexylmethyl)-amide | 100 | 70 | | | |
| Comparison compound methoxyethyl-mercury-silicate | | | 96 | 86 | 70 |

EXAMPLE 11

**Effect of seed treatment of wheat against *Tilletia caries***

Wheat seeds were contaminated with 3 g per kg of spores of the stinking smuts fungus *Tilletia caries*. Untreated grains as well as grain treated with the compounds listed below were then pressed with their tuft end into Petri dishes filled with moist loam and were incubated at temperatures below +12° C. for a period of 3 days. The grains were then removed and the Petri dishes with the remaining spores of the stinking smuts were further incubated at about +12° C.; after 10 days the spores were examined regarding germination. The fungicidal effect was calculated as follows:

$$100 - \frac{100 \cdot \text{germination percentage in treated plants}}{\text{germination percentage in untreated plants}} = \% \text{ activity}$$

The compounds were applied in the form of a 20% spray powder.

| Compounds | % action of 20 g active agent per 100 kg of seed material |
|---|---|
| 4-methyl-1,2,3-thiadiazole-5-carboxylic acid-(N-chloroacetyl-N-cyclohexylmethyl)-amide | 75 |
| 4-methyl-1,2,3-thiadiazole-5-carboxylic acid-(N-valeryl-N-cyclohexylmethyl)-amide | 75 |
| 4-methyl-1,2,3-thiadiazole-5-carboxylic acid-[N-(2,4-dichlorphenoxyacetyl)-N-cyclohexylmethyl]-amide | 75 |
| 4-methyl-1,2,3-thiadiazole-5-carboxylic acid-[N-(2-chlorobenzoyl)-N-cyclohexylmethyl]-amide | 84 |
| 4-methyl-1,2,3-thiadiazole-5-carboxylic acid-(N-cinnamoyl-N-cyclohexylmethyl)-amide | 80 |
| 4-methyl-1,2,3-thiadiazole-5-carboxylic acid-(N-cyclohexylcarbonyl-N-cyclohexylmethyl)-amide | 82 |
| 4-methyl-1,2,3-thiadiazole-5-carboxylic acid-(N-cyclohexylmethyl-N-cyclopropylcarbonyl)-amide | 90 |

EXAMPLE 12

Cotton leaves at the stage of 6-7 fully developed leaves were sprayed four times with the below listed compound as an aqueous emulsion or suspension in an amount of 500 l water/ha. The number of leaves dropped after 9 days is shown below as the percentage of the initial leaves.

| Compound | kg/ha | % defoliation |
|---|---|---|
| 4-methyl-1,2,3-thiadiazole-5-carboxylic acid-(N-acetyl-N-cyclohexylmethyl)-amide | 0.5 | 76.9 |
| Comparison compound | | |
| Tri-n-butyl-trithiophosphate | 0.5 | 65.4 |

EXAMPLE 13

Cotton plants at the stage of 5 to 6 fully developed foliage leaves were sprayed with the compounds listed below in the concentrations indicated. The compounds were applied in the form of an aqueous emulsion or suspension in amounts of 0.5 kg in 500 liter water/ha. The treatment was repeated 4 times. In the following table the dropped leaves were counted after 14 days as a percentage of all leaves existing when the treatment commenced.

| Compound | kg/ha | % leaf drop |
|---|---|---|
| 4-methyl-1,2,3-thiadiazole-5-carboxylic acid-(N-chloroacetyl)-amide | 0.5 | 81.0 |
| 4-methyl-1,2,3-thiadiazole-5-carboxylic acid-(N-valeryl-N-cyclohexylmethyl)-amide | 0.5 | 81.0 |
| 4-methyl-1,2,3-thiadiazole-5-carboxylic acid-(N-isobutyryl-N-cyclohexylmethyl)-amide | 0.5 | 66.7 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. 1,2,3-thiadiazole-5-carboxylic acid amide derivatives of the formula $$\begin{array}{c} N\text{———}C-R_1 \\ \| \quad \quad \| \\ N \diagdown_S \diagup C-CO-N-CO-R_3 \\ \quad \quad \quad \quad \quad | \\ \quad \quad \quad \quad \quad R_2 \end{array}$$

wherein
$R_1$ is methyl,
$R_3CO$ is acetyl, crotonyl, chloroacetyl, dichloroacetyl, propionyl, isobutyryl, valeryl, cinnamoyl, furoyl, 4-methyl-1,2,3-thiadiazol-5-ylcarbonyl, cyclopropylcarbonyl, cyclohexylcarbonyl, dichlorophenoxyacetyl, phenoxybenzoyl, benzoyl, halobenzoyl, dichlorobenzoyl, dichloromethoxybenzoyl, methylbenzoyl or trifluoromethylbenzoyl, and
$R_2$ is benzyl, halobenzyl, cyclohexyl, methylcyclohexyl or cyclohexylmethyl.

2. The compounds of claim 1 wherein
$R_1$ is methyl
$R_3CO$ is acetyl, chloroacetyl, propionyl, valeryl, cinnamoyl, cyclohexylcarbonyl, dichlorophenoxyacetyl, benzoyl, halobenzoyl, dichlorobenzoyl or methylbenzoyl, and
$R_2$ is benzyl, halobenzyl, cyclohexyl, methylcyclohexyl or cyclohexylmethyl.

3. The compound of claim 1 which is 4-methyl-1,2,3-thiadiazole-5-carboxylic acid-(N-acetyl-N-cyclohexylmethyl)-amide.

4. The compound of claim 1 which is 4-methyl-1,2,3-thiadiazole-5-carboxylic acid-(N-benzoyl-N-cyclohexylmethyl)-amide.

5. The compound of claim 1 which is 4-methyl-1,2,3-thiadiazole-5-carboxylic acid-(N-isobutyryl-N-cyclohexylmethyl)-amide.

6. The compound of claim 1 which is 4-methyl-1,2,3-thiadiazole-5-carboxylic acid-(N-benzonyl-N-benzyl)-amide.

7. The compound of claim 1 which is 4-methyl-1,2,3-thiadiazole-5-carboxylic acid-[N-benzoyl-N-(4-fluorobenzyl)]-amide.

8. The compound of claim 1 which is 4-methyl-1,2,3-thiadiazole-5-carboxylic acid-[N-benzoyl-N-(2-methylcyclohexyl)]-amide.

9. The compound of claim 1 which is 4-methyl-1,2,3-thiadiazole-5-carboxylic acid-[N-acetyl-N-(2-fluorobenzyl)]-amide.

10. The compound of claim 1 which is 4-methyl-1,2,3-thiadiazole-5-carboxylic acid-[N-acetyl-N-(4-fluorobenzyl)]-amide.

11. The compound of claim 1 which is 4-methyl-1,2,3-thiadiazole-5-carboxylic acid-[N-acetyl-N-(4-chlorobenzyl)]-amide.

12. The compound of claim 1 which is 4-methyl-1,2,3-thiadiazole-5-carboxylic acid-[N-(4-chlorobenzoyl)-N-cyclohexylmethyl]-amide.

13. The compound of claim 1 which is 4-methyl-1,2,3-thiadiazole-5-carboxylic acid-(N-propionyl-N-cyclohexylmethyl)-amide.

14. The compound of claim 1 which is 4-methyl-1,2,3-thiadiazole-5-carboxylic acid-[N-(4-fluorobenzoyl)-N-cyclohexylmethyl]-amide.

15. The compound of claim 1 which is 4-methyl-1,2,3-thiadiazole-5-carboxylic acid-(N-chloroacetyl-N-cyclohexylmethyl)-amide.

16. The compound of claim 1 which is 4-methyl-1,2,3-thiadiazole-5-carboxylic acid-[N-(3-chlorobenzoyl)-N-cyclohexylmethyl]-amide.

17. The compound of claim 1 which is 4-methyl-1,2,3-thiadiazole-5-carboxylic acid-[N-(3-methylbenzoyl)-N-cyclohexylmethyl]-amide.

18. The compound of claim 1 which is 4-methyl-1,2,3-thiadiazole-5-carboxylic acid-[N-(4-methylbenzoyl)-N-cyclohexylmethyl]-amide.

19. The compound of claim 1 which is 4-methyl-1,2,3-thiadiazole-5-carboxylic acid-(N-valeryl-N-cyclohexylmethyl)-amide.

20. The compound of claim 1 which is 4-methyl-1,2,3-thiadiazole-5-carboxylic acid-[N-(2,4-dichlorophenoxyacetyl)-N-cyclohexylmethyl]-amide.

21. The compound of claim 1 which is 4-methyl-1,2,3-thiadiazole-5-carboxylic acid-(N-benzoyl-N-cyclohexyl)-amide.

22. The compound of claim 1 which is 4-methyl-1,2,3-thiadiazole-5-carboxylic acid-(N-acetyl-N-cyclohexyl)-amide.

23. The compound of claim 1 which is 4-methyl-1,2,3-thiadiazole-5-carboxylic acid-[N-(2-chlorobenzoyl)-N-cyclohexylmethyl]-amide.

24. The compound of claim 1 which is 4-methyl-1,2,3-thiadiazole-5-carboxylic acid-(N-cinnamoyl-N-cyclohexylmethyl)-amide.

25. The compound of claim 1 which is 4-methyl-1,2,3-thiadiazole-5-carboxylic acid-(N-cyclohexylcarbonyl-N-cyclohexylmethyl)-amide.

26. The compound of claim 1 which is 4-methyl-1,2,3-thiadiazole-5-carboxylic acid-(N-cyclohexylmethyl-N-cyclopropylcarbonyl)-amide.

27. The compound of claim 1 which is 4-methyl-1,2,3-thiadiazole-5-carboxylic acid-[N-cyclohexylmethyl-N-(2,6-dichlorobenzoyl)]-amide.

28. The compound of claim 1 which is 4-methyl-1,2,3-thiadiazole-5-carboxylic acid-(N-cyclohexylmethyl-N-dichloroacetyl)-amide.

29. The compound of claim 1 which is 4-methyl-1,2,3-thiadiazole-5-carboxylic acid-(N-crotonoyl-N-cyclohexylmethyl)-amide.

30. The compound of claim 1 which is 4-methyl-1,2,3-thiadiazole-5-carboxylic acid-[N-cyclohexylmethyl-N-(2-furoyl)]-amide.

31. The compound of claim 1 which is 4-methyl-1,2,3-thiadiazole-5-carboxylic acid-[N-cyclohexylmethyl-N-(2,4-dichlorobenzoyl)]-amide.

32. The compound of claim 1 which is 4-methyl-1,2,3-thiadiazole-5-carboxylic acid-[N-cyclohexylmethyl-N-(2-trifluoromethylbenzoyl)]-amide.

33. The compound of claim 1 which is 4-methyl-1,2,3-thiadiazole-5-carboxylic acid-[N-cyclohexylmethyl-N-(3,6-dichloro-2-methoxybenzoyl)]-amide.

34. The compound of claim 1 which is 4-methyl-1,2,3-thiadiazole-5-carboxylic acid-[N-cyclohexylmethyl-N-(3-trifluoromethylbenzoyl)]-amide.

35. The compound of claim 1 which is 4-methyl-1,2,3-thiadiazole-5-carboxylic acid-[N-cyclohexylmethyl-N-(3-furoyl)]-amide.

36. The compound of claim 1 which is 4-methyl-1,2,3-thiadiazole-5-carboxylic acid-[N-cyclohexylmethyl-N-(2,5-dichlorobenzoyl)]-amide.

37. The compound of claim 1 which is 4-methyl-1,2,3-thiadiazole-5-carboxylic acid-[N-cyclohexylmethyl-N-(3,5-dichlorobenzoyl)]-amide.

38. The compound of claim 1 which is 4-methyl-1,2,3-thiadiazole-5-carboxylic acid-[N-cyclohexylmethyl-N-(2-phenoxybenzoyl)]-amide.

39. The compound of claim 1 which is 4-methyl-1,2,3-thiadiazole-5-carboxylic acid-[N-cyclohexylmethyl-N-(4-methyl-1,2,3-thiadiazole-5-ylcarbonyl)]-amide.

40. The compound of claim 1 which is 4-methyl-1,2,3-thiadiazole-5-carboxylic acid-[N-cyclohexylmethyl-N-(3,4-dichlorobenzoyl)]-amide.

41. The compound of claim 1 which is 4-methyl-1,2,3-thiadiazole-5-carboxylic acid-[N-acetyl-N-(3-methylcyclohexyl)]-amide.

42. A composition having herbicidal, growth regulating and defoliating activity in which at least one of the active agents is a compound as defined in claim 1, the said active agent being present in amounts of about 5 to 95% by weight, the composition including about 95 to 5% by weight of liquid or solid carrier materials.

43. The composition of claim 42 which includes up to 20% by weight of surface active agents with a corresponding reduction of the amount of liquid or solid carrier materials.

44. A composition having fungicidal activity comprising at least one active agent as defined in claim 1 in amounts of about 5 to 90% by weight, liquid or solid carrier materials being present in an amount of about 95 to 5% by weight.

45. The composition of claim 44 which includes up to 20% of surface active agents with a corresponding reduction of the liquid or solid carrier materials.

* * * * *